(12) United States Patent
Ren et al.

(10) Patent No.: US 11,464,472 B2
(45) Date of Patent: *Oct. 11, 2022

(54) X-RAY IMAGING WITH X-RAY MARKERS THAT PROVIDE ADJUNCT INFORMATION BUT PRESERVE IMAGE QUALITY

(71) Applicant: Hologic, Inc., Marlborough, MA (US)

(72) Inventors: Baorui Ren, Andover, MA (US); Andrew P. Smith, Lexington, MA (US); Zhenxue Jing, Chads Ford, PA (US); Jay Stein, Boston, MA (US); Kenneth F. Defreitas, Patterson, NY (US)

(73) Assignee: Hologic, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/174,708

(22) Filed: Feb. 12, 2021

(65) Prior Publication Data

US 2021/0204894 A1 Jul. 8, 2021

Related U.S. Application Data

(63) Continuation of application No. 16/515,448, filed on Jul. 18, 2019, now Pat. No. 10,952,692, which is a (Continued)

(51) Int. Cl.
 *A61B 6/00* (2006.01)
 *A61B 6/04* (2006.01)
 *A61B 5/107* (2006.01)

(52) U.S. Cl.
 CPC .......... *A61B 6/502* (2013.01); *A61B 6/0414* (2013.01); *A61B 6/544* (2013.01); *A61B 5/1075* (2013.01); *A61B 6/583* (2013.01)

(58) Field of Classification Search
 CPC ..... A61B 6/502; A61B 6/0414; A61B 6/0421; A61B 6/544
 See application file for complete search history.

(56) References Cited

U.S. PATENT DOCUMENTS

| 4,496,557 A | 1/1985 | Malen et al. |
| 4,597,094 A | 6/1986 | Kleinman |
| (Continued) |

FOREIGN PATENT DOCUMENTS

| EP | 0982001 | 3/2000 |
| JP | 2005021345 | 1/2022 |
| (Continued) |

OTHER PUBLICATIONS

Aug. 17, 2007 European search report in connection with corresponding European patent application No. EP 06 25 5790, 13 pgs.
(Continued)

*Primary Examiner* — Chih-Cheng Kao
(74) *Attorney, Agent, or Firm* — Merchant & Gould P.C.

(57) ABSTRACT

A method and an apparatus for estimating a geometric thickness of a breast in mammography/tomosynthesis or in other x-ray procedures, by imaging markers that are in the path of x-rays passing through the imaged object. The markings can be selected to be visible or to be invisible when the composite markings/breast image is viewed in clinical settings. If desired, the contribution of the markers to the image can be removed through further processing. The resulting information can be used determining the geometric thickness of the body being x-rayed and thus setting imaging parameters that are thickness-related, and for other purposes. The method and apparatus also have application in other types of x-ray imaging.

18 Claims, 14 Drawing Sheets

Related U.S. Application Data continuation of application No. 14/312,434, filed on Jun. 23, 2014, now Pat. No. 10,398,398, which is a continuation of application No. 12/150,539, filed on Apr. 28, 2008, now Pat. No. 8,768,026, which is a continuation-in-part of application No. 11/827,909, filed on Jul. 13, 2007, now Pat. No. 7,616,801, which is a continuation-in-part of application No. 11/271,050, filed on Nov. 11, 2005, now Pat. No. 7,577,282, which is a continuation-in-part of application No. 10/723,486, filed on Nov. 26, 2003, now Pat. No. 7,831,296.

(56) References Cited

U.S. PATENT DOCUMENTS

| | | |
|---|---|---|
| 4,905,150 A | 2/1990 | Aichinger |
| 4,962,515 A | 10/1990 | Kopans |
| 5,051,904 A | 9/1991 | Griffith et al. |
| 5,359,637 A | 10/1994 | Webber |
| 5,479,927 A | 1/1996 | Shmulewitz |
| 5,668,844 A | 9/1997 | Webber |
| 5,872,828 A | 2/1999 | Niklason et al. |
| 5,941,832 A | 8/1999 | Tumey et al. |
| 5,957,762 A | 9/1999 | Schreifer |
| 5,986,662 A | 11/1999 | Argiro et al. |
| 6,049,583 A | 4/2000 | Galkin |
| 6,141,398 A | 10/2000 | He et al. |
| 6,219,059 B1 | 4/2001 | Argiro |
| 6,289,235 B1 | 9/2001 | Webber |
| 6,292,530 B1 | 9/2001 | Yavus et al. |
| 6,411,836 B1 | 6/2002 | Patel et al. |
| 6,487,271 B1 | 11/2002 | Laurent |
| 6,529,575 B1 | 3/2003 | Hsieh |
| 6,574,304 B1 | 6/2003 | Hsieh et al. |
| 6,597,762 B1 | 7/2003 | Ferrant et al. |
| 6,633,674 B1 | 10/2003 | Barnes et al. |
| 6,647,092 B2 | 11/2003 | Eberhard et al. |
| 6,652,142 B2 | 11/2003 | Launay et al. |
| 6,744,848 B2 | 6/2004 | Stanton et al. |
| 6,751,285 B2 | 6/2004 | Eberhard et al. |
| 6,882,700 B2 | 4/2005 | Wang et al. |
| 6,885,724 B2 | 4/2005 | Li et al. |
| 6,912,319 B1 | 6/2005 | Barnes et al. |
| 6,940,943 B2 | 9/2005 | Claus et al. |
| 6,999,554 B2 | 2/2006 | Mertelmeir |
| 7,110,490 B2 | 9/2006 | Eberhard et al. |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,245,694 B2 | 7/2007 | Jing et al. |
| 7,323,692 B2 | 1/2008 | Rowlands et al. |
| 7,577,282 B2 | 8/2009 | Gkanatsios et al. |
| 7,616,801 B2 | 11/2009 | Gkanatsios et al. |
| 7,760,924 B2 | 7/2010 | Ruth et al. |
| 7,831,296 B2 | 11/2010 | DeFrietas et al. |
| 7,916,915 B2 | 3/2011 | Gkanatsios et al. |
| 8,768,026 B2 | 7/2014 | Ren et al. |
| 10,398,398 B2 | 9/2019 | Ren et al. |
| 10,952,692 B2 * | 3/2021 | Ren ..................... A61B 6/544 |
| 2001/0038681 A1 | 11/2001 | Stanton et al. |
| 2002/0050986 A1 | 5/2002 | Inoue et al. |
| 2002/0131559 A1 | 9/2002 | Launay et al. |
| 2003/0026386 A1 | 2/2003 | Tang et al. |
| 2003/0043962 A1 | 3/2003 | Lai |
| 2003/0072409 A1 | 4/2003 | Kaufhold et al. |
| 2003/0095624 A1 | 5/2003 | Eberhard et al. |
| 2003/0169847 A1 | 9/2003 | Karrellas et al. |
| 2003/0194121 A1 | 10/2003 | Eberhard et al. |
| 2003/0210254 A1 | 11/2003 | Doan et al. |
| 2003/0212327 A1 | 11/2003 | Wang et al. |
| 2003/0215120 A1 | 11/2003 | Uppaluri et al. |
| 2004/0066884 A1 | 4/2004 | Claus et al. |
| 2004/0094167 A1 | 5/2004 | Brady et al. |
| 2004/0109529 A1 | 6/2004 | Eberhard et al. |
| 2004/0264648 A1 | 12/2004 | Claus et al. |
| 2005/0084062 A1 | 4/2005 | Andreasson et al. |
| 2005/0105679 A1 | 5/2005 | Wu et al. |
| 2005/0113681 A1 | 5/2005 | DeFrietas et al. |
| 2005/0129172 A1 | 6/2005 | Mertelmeir |
| 2005/0135555 A1 | 6/2005 | Claus et al. |
| 2005/0135664 A1 | 6/2005 | Kaufhold et al. |
| 2005/0226375 A1 | 10/2005 | Eberhard et al. |
| 2006/0058603 A1 | 3/2006 | Dave |
| 2006/0098855 A1 | 5/2006 | Gkanatsios et al. |
| 2007/0036265 A1 | 2/2007 | Jing et al. |
| 2007/0217667 A1 | 9/2007 | Maack |
| 2007/0242797 A1 | 10/2007 | Stewart et al. |
| 2009/0141859 A1 | 6/2009 | Gkanatsios et al. |
| 2009/0268865 A1 | 10/2009 | Ren et al. |
| 2010/0135558 A1 | 6/2010 | Ruth et al. |
| 2010/0246759 A1 | 9/2010 | Ogura |
| 2011/0069808 A1 | 3/2011 | DeFrietas et al. |
| 2011/0135185 A1 | 6/2011 | Gkanatsios et al. |
| 2014/0301529 A1 | 10/2014 | Ren et al. |

FOREIGN PATENT DOCUMENTS

| | | |
|---|---|---|
| WO | WO 98/16903 | 4/1998 |
| WO | WO 03/020114 | 3/2022 |
| WO | WO 2005/051197 | 6/2022 |
| WO | WO 2006/058160 | 6/2022 |

OTHER PUBLICATIONS

Berks et al., "Feasibility and Acceptability of Stepwedge-Based Density Measurement", Jun. 21, 2006, IWDM 2006, LNCS vol. 4046, pp. 355-361.

Burch et al., "A method for estimating compressed breast thickness during mammography", 1995, The British Journal of Radiology, vol. 68, pp. 394-399.

Diffey et al., Quantifying Breast Thickness for Density Measurement, Jul. 23, 2008, IWDM 2008, LNCS 5116, pp. 651-658.

Digital Clinical Reports, Tomosynthesis, GE Brochure 98-5493, Nov. 1998.

Federica Pediconi et al., "Color-coded automated signal intensitycurve for detection and characterization of breast lesions: Preliminary evaluation of a new software for MR-based breast imaging", International Congress Series 1281 (2005) 1081-1086.

Heang-Ping Chan et al., "ROC study of the effect of stereoscopic imaging on assessment of breast lesions", Medical Physics, vol. 32, No. 4, Apr. 2005.

Hufton et al., A Method for the Quantification of Dense Breast Tissue from Digitized Mammograms, Jun. 2004, 2004 International Workshop on Digital Mammography, pp. 430-435.

Jeffreys et al., "Initial experiences of using an automated volumetric measure of breast density: the standard mammogram form", Br J Radiol. May 2006 ;79 (941):378-82, 16632617.

Lorad Selenia™ Document B-BI-SEO US/Intl (May 2006), copyright Hologic 2006.

Navab, Nassir et al. "Dynamic geometrical calibration for 3D cerebral angiography", SPIE vol. 2708, Jan. 10, 2010, pp. 361-370.

PCT International Search Report in International Patent Application No. PCT/US2005/041941, dated Sep. 25, 2008, 2 pgs., related to copending U.S. Appl. No. 11/667,650.

Vacek, Pamela et al., "A Prospective Study of Breast Cancer Risk Using Routine Mammographic Breast Density Measurements", Cancer Epidemiology Biomarkers & Prevention, vol. 13, No. 5, pp. 715-722, May 2004, American Association for Cancer Research.

Vacek, Pamela, "Cancer Epidemiology Biomarkers & Prevention", vol. 13, 715-722, May 2004, American Association for Cancer Research.

* cited by examiner

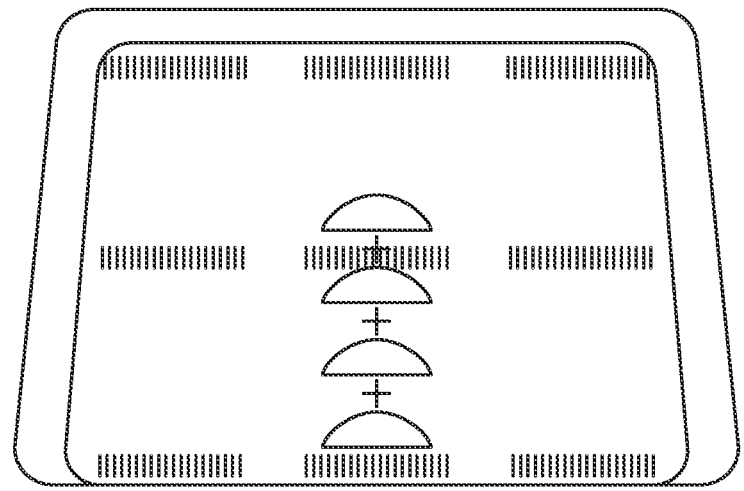
Fig. 5c
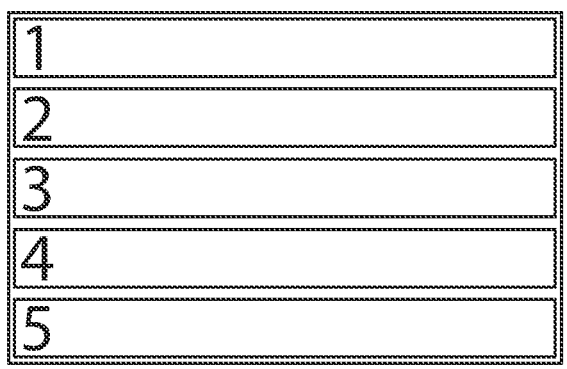 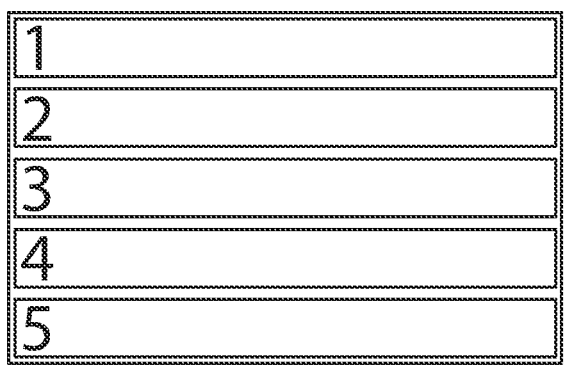
Fig. 6a	Fig. 6b

X-RAY IMAGING WITH X-RAY MARKERS THAT PROVIDE ADJUNCT INFORMATION BUT PRESERVE IMAGE QUALITY

CROSS REFERENCE OF RELATED APPLICATIONS

This application is a continuation of U.S. patent application Ser. No. 16/515,448, filed Jul. 18, 2019, now U.S. Pat. No. 10,952,692; which is a continuation of U.S. patent application Ser. No. 14/312,434, filed Jun. 23, 2014, now U.S. Pat. No. 10,398,398; which is a continuation of U.S. patent application Ser. No. 12/150,539, filed Apr. 28, 2008, now U.S. Pat. No. 8,768,026; which is a continuation-in-part of U.S. patent application Ser. No. 11/827,909, filed Jul. 13, 2007, now U.S. Pat. No. 7,616,801; which is a continuation-in-part of U.S. patent application Ser. No. 11/271,050, filed Nov. 11, 2005, now U.S. Pat. No. 7,577,282; which is a continuation-in-part of U.S. patent application Ser. No. 10/723,486, filed Nov. 26, 2003, now U.S. Pat. No. 7,831,296; the disclosures of which are hereby incorporated by reference in their entireties.

TECHNICAL FIELD

This patent specification relates to x-ray imaging and more specifically to accurately finding the geometric thickness of an object being x-rayed through including markers in the x-ray path and computer-processing the composite markers/object x-ray image to identify the markers and to use the resulting information to calculate geometric object thickness and improve imaging.

BACKGROUND

Breast cancer and other breast lesions continue to be a significant threat to women's health. X-ray mammography currently is the most widely used tool for early detection and diagnosis, and is the modality approved by the U.S. Food and Drug Administration to screen for breast cancer in women who do not show symptoms of breast disease. A typical x-ray mammography system compresses and immobilizes a patient's breast on a breast platform positioned between an x-ray source and an x-ray imager, and takes a projection x-ray image (called here a conventional mammogram or simply mammogram) using a collimated cone or pyramid beam of x-rays at appropriate factors such as mA (current), kVp (voltage) or keV (energy), and msec (exposure time). In the United States, typically two views are taken of each breast, one from above (cranial-caudal, or CC, with the image plane generally at a 0° angle to the horizontal and one from the side (mediolateral-oblique, or MLO, with the image plane at an angle of typically around 45° to the horizontal). Different typical views may be taken in other countries. The x-ray source typically is an x-ray tube operating at or in the neighborhood of 25-30 kVp, using a molybdenum, rhodium, or tungsten rotating anode with a focal spot of about 0.3 to 0.4 mm and, in some cases, 0.1 mm or less. An anti-scatter grid between the breast and the imager can be used to reduce the effects of x-ray scatter. The breast is compressed to reduce patient motion and also for reasons such as reducing scatter, separating overlapping structures in the breast, reducing the x-ray thickness of the imaged breast and making it more uniform, and providing more uniform x-ray exposure. Traditionally, the imager has been a film/screen unit in which the x-rays impinging on the screen generate light that exposes the film. In the last several years, mammography systems using electronic digital flat panel array receptors have made significant inroads. A Selenia™ digital mammography system with such a digital flat panel x-ray receptor or imager is offered by Lorad, a division of the assignee hereof, Hologic, Inc. of Bedford, Mass. See brochure "Lorad Selenia™" Document B-BI-SEO US/Intl (5/06) copyright Hologic 2006. Digital mammography has significant advantages and in time may fully supplant film/screen systems. Additional information regarding digital mammography systems and processes offered by the common assignee can be found at <www.hologic.com>. Digital tomosynthesis also has made advances and the assignee hereof has exhibited breast tomosynthesis systems at trade shows and has carried out clinical testing. It is a three-dimensional process in which several two-dimensional projection views are acquired at respective different angles but lower x-ray dose than conventional mammograms, and are reconstructed into tomosynthesis slice views that can be along any desired plane in the breast. For tomosynthesis, the breast is still immobilized but may be compressed to the same or lesser extent than in conventional mammography. See, e.g., International Application WO 2006/058160 A2 published under the Patent Cooperation Treaty on Jun. 1, 2006 and Patent Application Publication No. 2001/0038681 A, PCT application International Publication No. WO 03/020114 A2 published Mar. 13, 2003, U.S. Pat. Nos. 7,142,633, 6,885,724, 6,647,092, 6,289,235, 5,051,904, 5,359,637, and 4,496,557, and published patent applications US 2004/0109529 A1, US 2004/0066884 A1, US 2005/0105679 A1, US 20050129172A1, and Digital Clinical Reports, Tomosynthesis, GE Brochure 98-5493, 11/98. Reference markers can be used in x-ray imaging for purposes such as checking the rotation angle and unwanted shift of center of rotation of an x-ray source and receptor (imager), and fiducial phantoms can be used in 3D angiography to calibrate for irregular scan geometries. See, e.g., U.S. Pat. Nos. 5,051,904, 5,359,637, and 6,289,235, N. Navab, et al., Dynamic geometrical calibration for 3D cerebral anglography, SPIE Vol. 2708, pp. 361 370, and said PCT published application WO 03/020114 A2. A tomosynthesis system specifically for imaging patients' breast is disclosed in commonly owned U.S. Pat. Nos. 7,123,684 and 7,245,694. The same system can be selectively used for mammography and tomography, in the same or different compressions of the patient's breast.

It is desirable to know the geometric thickness of the immobilized breast in both film/screen and digital flat panel x-ray mammography as well as in tomosynthesis in order to make appropriate setting for the imaging procedure, such as settings for the x-ray tube that control the x-ray beam. Knowing the breast thickness can also help in quantitative assessments regarding x-ray images of the breast, such as in assessing the nature and clinical significance of x-ray attenuation properties of the breast. It can also be used in tomosynthesis reconstructions such as to determine the required reconstructed field of view or desired display field of view. It has been proposed to use encoders to measure the geometric height of a breast compression paddle and use the result to estimate the geometric thickness of the breast but this process typically has a relatively high error because of factors such as tilting and geometric distortions of the paddle as it compresses the breast, and because the encoders must be calibrated. The information on the paddle height is oftentimes stored in the DICOM header associated with the medical image, and this information is used for several purposes, including the calculation of body part radiation exposure. It also has been proposed to derive breast thickness information from measuring the paddle compression force versus time and to use the results to guide control factors such as kV, mAs, and filter selection, as in commonly assigned U.S. Pat. No. 7,123,684. The geometric thickness of any other body part being x-rayed also can be of interest, and one process for basing an estimate on non-contact ranging using ultrasound is discussed in U.S. Pat. No. 4,597,094. It has also been proposed to use a calibration phantom with embedded pellets of high-density material serving as markers and to use the imaged markers in calibrating the system, such as once a week. See U.S. Pat. No. 7,142,633 cited above.

Proposals have been made for automated methods of estimating breast density from mammograms, including volumetric and areal estimates. One example, using digitized film mammograms, is given in Br J Radiol. 2006 May; 79 (941):378-82 1663217. These methods are understood to derive the volume of fibroglanduar tissue in the breast tissue for a cross-sectional area in a mammogram. The accuracy of these methods is believed to be related to the accuracy of measurement of the actual compressed breast, in addition, information has been published proposing that breast density is related to the breast cancer risk, See Cancer Epidemiology Biomarkers & Prevention, Vol 13, 715-722, May 2004, American Association for Cancer Research.

The patents and other publications identified above, including the brochure "Lorad Selenia™" and said published application WO 20061058160 (corresponding U.S. patent application Ser. No. 11/791,601), are hereby incorporated by reference in this patent specification.

SUMMARY OF DISCLOSURE

In one non-limiting example, a breast imaging method comprises x-ray imaging a pattern of markers on a compression paddle and a patient's breast immobilized between the paddle and an x-ray imaging receptor to form a composite x-ray image in which the x-ray image of markers is composited with the x-ray image of the breast, computer-processing the composite x-ray image to derive geometric information regarding the imaged markers, computer-processing the geometric information to derive thickness information related to a thickness of the immobilized breast or other information related to the position of the pattern of markers in space or relative to system components, and using the thickness or spatial position information for improving breast imaging. The imaged markers may be invisible within the breast outline when viewing the composite image in typical clinical settings or, in alternative embodiments, they may be visible in the composite image. The method can further include removing some or essentially all the contribution of the markers from the composite x-ray image.

As another non-limiting example, an apparatus comprises a compression paddle with a pattern of markers that immobilizes a patient's breast against a breast platform, an x-ray source on one side of the paddle and platform and an x-ray imaging receptor on the other side, a processor receiving image information from the receptor related to a composite x-ray image of the markers and breast in which the markers are not visible in a clinical setting, said processor computer-processing the composite image to derive geometric information regarding the markers therein and computer-processing the geometric information to derive thickness information related to thickness of the immobilized breast, and said processor using the thickness information to improve imaging the breast. The processor can further process the composite image to completely or essentially remove some or essentially all contribution of the imaged markers.

The method and the apparatus can be applied to both mammography and tomosynthesis systems, and the term "mammography/tomosynthesis" is used in this patent specification to mean any one of a mammography system, a tomosynthesis system, and a fusion system that can selectively carry one or both of mammography and tomosynthesis, including while a patients breast remains immobilized.

In addition to or instead of being on the compression paddle, similar markers can be placed on other objects. For example, markers can be placed on the magnification table that is placed between the normal breast platform and the breast to increase the distance between the breast and the imaging plane and thus magnify the breast image. Markers can be placed on the normal breast platform if it desirable to calculate or confirm the spacing between the breast platform and the image plane. In general, markers can be placed on any object that is between the x-ray tube and the image plane of the x-ray receptor to help calculate the distance between the object and the image plane or other objects.

A pattern of parallel lines, like the mm marks of a ruler, can be used as the pattern of markings. However, many other patterns of markings can be used and may be preferable depending on the goals of the measurement. For example, a pattern can be dots or a distributed collection of short increments of lines that will be imaged as very small areas that are well dispersed in the x-ray image. The distribution can even be pseudo-random, to further help in making the imaged pattern invisible in clinical settings, so long as the pattern has properties that can help find it when imaged in the x-ray image; for example the pattern is known, or has enough sharp edges that can differentiate the pattern elements from background breast images through suitable edge detection of other computer processing, if the markers in a pattern are elongated, they can be at any desired orientation.

While this patent specification discusses, as one alternative, patterns of markings that when imaged are invisible in the composite x-ray image when viewed in typical clinical settings, it also explains an alternative in which the imaged markers are visible in the composite image when viewed in clinical settings. In the first alternative, the x-ray attenuation properties of the patterns of markers can have values that are insufficient to make the imaged markers visible in clinical settings but sufficient to allow them to be identified through computer processing. In the second alternative, the pattern of markers may have sufficient x-ray attenuation to make the imaged markers visible in the composite image in typical clinical settings; however image processing can process the composite image to remove some or essentially all contribution of the imaged markers. Even when the imaged markers are invisible in the composite image in typical clinical settings, their contributions to the composite image can be removed through further computer processing to reduce possible interference with image processing such as CAD (computer aided detection). Another example of the patterns of markers arises in systems capable of tomosynthesis imaging. Tomosynthesis examinations acquire of raw, or projection images, and subsequently reconstruction them into tomosynthesis slice images that can be desired orientations and represent breast slices of desired thicknesses. Because the radiological assessment is typically made from the reconstructed slice images, patterns of markings and analysis as described in this patent specification are useful even if they are visible in the tomosynthesis projection images. This is because their contrast and visibility will be greatly reduced in the reconstructed slices that encompass the breast volume, because the patterns are physically located outside the breast. Because these examples relax the requirement for complete invisibility, additional uses become practical. In a typical digital mammography or tomosynthesis examination, the setting of x-ray exposure techniques are determined through the use of Automatic Exposure Control (AEC) methods, which typically use a low dose x-ray pre-pulse. The low doses employed in the pre-pulse means that the visibility of patterns of markings is reduced and so their contrast will need to be increased accordingly. Patterns of markings and methods according to this patent specification can be used when the appearance of the imaged markers is reduced through image processing, or when the imaged markers do not appear in the breast images of interest because those images are tomosynthesis reconstructed images representing slices of the breast while the imaged markings would mainly influence reconstructed images (if any) of slices outside the breast volume.

As yet another non-limiting example, computer software stored in a tangible storage medium can control an x-ray system to carry out implementation of the process described in this patent specification. Information such as breast thickness, paddle height and paddle deformation so obtained can be stored in the DICOM header associated with the medical image for subsequent uses.

The process and apparatus are not limited to applications for breast imaging but are applicable to other x-ray procedures as well.

BRIEF DESCRIPTION OF THE DRAWINGS

The features of the subject matter of this patent specification can be more readily understood from the following detailed description with reference to the accompanying drawings wherein:

FIG. 5c illustrates the compression paddle with an added example of a pattern (a ruler pattern as in FIG. 5a) for use with an embodiment of the disclosed process;

FIGS. 6a and 6b pertain to x-ray images taken with a compression paddle and ruler as in FIG. 5c, compressing a 4.5 cm thick BR50/50 phantom (BR50/50 is material simulating a breast comprised of 50% fatty and 50% glandular tissue, such as sold by Cirs Inc Model 014A Mammography Phototimer Consistency Testing Slabs, available from CIRS in Norfolk, Va., see http://www.cirsinc.com/pdfs/014Acp.pdf) in the case of FIG. 6a but a 4.5 cm thick cadaver breast phantom in the case of FIG. 6b. In each of FIGS. 6a and 6b: strip 1 illustrates a raw x-ray image of pattern and phantom/breast; strip 2 illustrates a pattern-corrected image obtained by removing the image of the pattern from the image of strip 1; strip 3 illustrates a difference image obtained by subtracting the strip 2 image from the strip 1 image; strip 4 illustrates a shift-and-add image of raw image 1 where the shift is at the correct distance and thus the imaged pattern of bars appears in the strip 4 image as an interference signal that is being detected; and strip 5 illustrates a shift-and-add image of image 2 where the shift also is at the correct distance but no interference signal is visible, demonstrating that the pattern that was present in strip 1 has been removed through pattern correction processing;

DETAILED DESCRIPTION OF PREFERRED EMBODIMENTS

Figure 1:
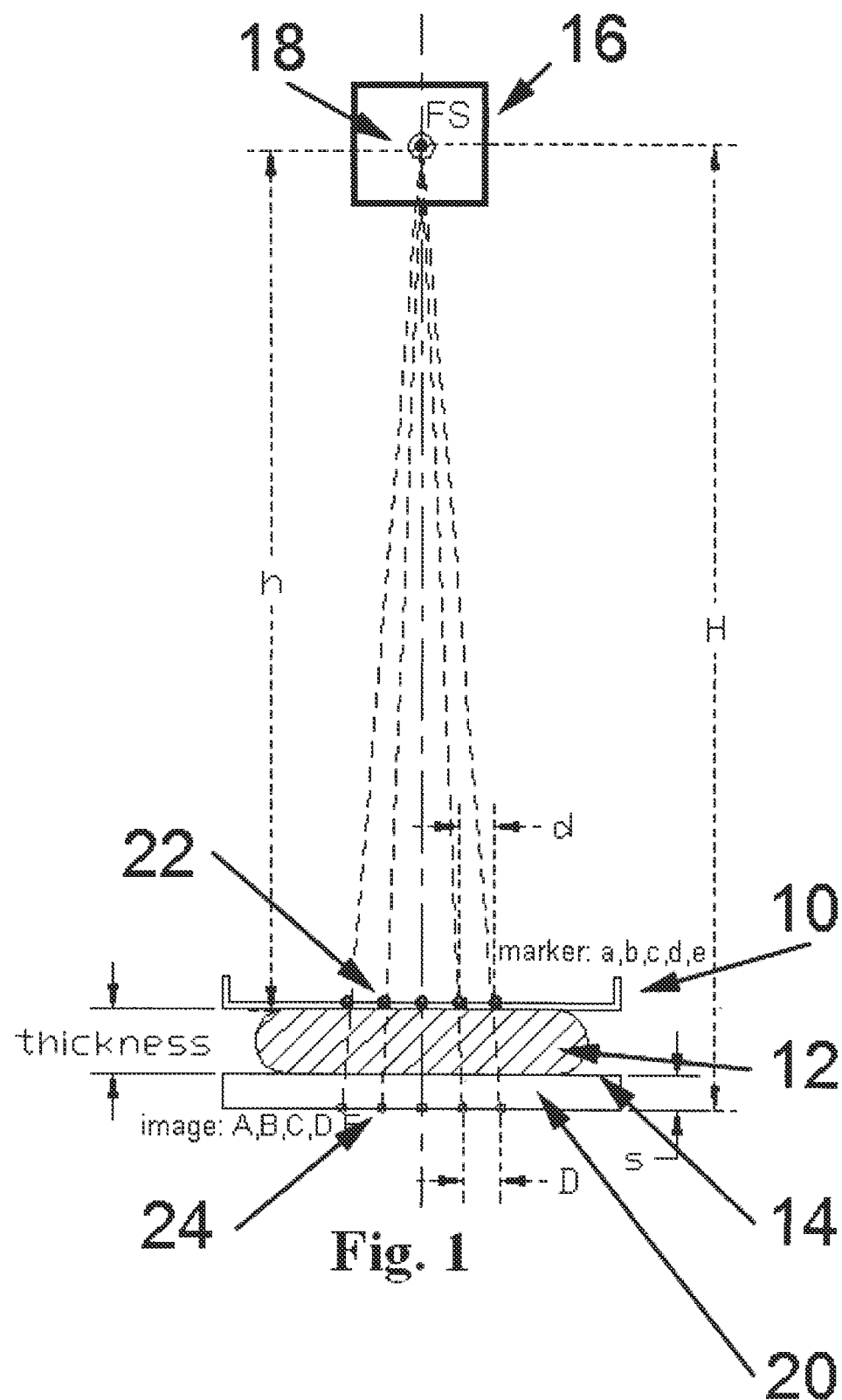
FIG. 1 is a schematic sectional view illustrating a geometry useful in estimating a thickness of a patient's breast immobilized between a compression paddle that has a pattern of markers and a breast platform, when imaged with x-rays in accordance with one embodiment of the present patent specification.

This patent specification describes methods and systems in which the geometric thickness of a body part such as the breast that is being x-rayed is accurately determined and used to improve imaging in a manner that does not inconvenience the patient or the health professional. It also describes similar processes to determine other thicknesses, heights, or distances between objects in x-ray examination procedures.

In describing preferred embodiments illustrated in the drawings, specific terminology is employed for the sake of clarity. However, this patent specification is not intended to be limited to the specific terminology so selected and it is to be understood that each specific element includes all technical equivalents that operate in a similar manner. In addition, a detailed description of known functions and configurations will be omitted when it may obscure the subject matter of the invention described in the appended claims.

As illustrated in the example of FIG. 1, a mammography or tomosynthesis system immobilizes a patients breast 12 between a compression paddle 10 and a breast platform 14. An x-ray source 16 when energized emits x-rays from a focal spot 18 that pass through paddle 10, breast 12 and platform 14 and are imaged at an imaging plane of an imaging receptor 20 that is below platform 14 and may for some x-ray procedures be separated therefrom by an anti-scatter grid not shown in FIG. 1. A pattern 22 of five markers "a, b, c, d, e" is formed in or on paddle 10 and is imaged by the x-rays as respective imaged markers "A, B, C, D, E" in the projection breast image formed at the imaging plane of receptor 20. The overall geometry of a mammography/tomosynthesis system to which the arrangement of FIG. 1 can be added is described in said published application WO 2006/058160.

It can be appreciated that if the geometry of markers 22 is known and the geometry of imaged markers 24 is measured in the x-ray image, trigonometric calculations can yield the distance between markers 22 and the imaging plane. The distance between markers 22 and the bottom of compression paddle 10, and the distance between the imaging plane and the top of breast platform are known. These distances are sufficient to calculate the geometric thickness of immobilized breast 12. An additional challenge arises in cases where it is not acceptable or desirable to have an easily visible contribution of the imaged markers to the composite x-ray image. For example, it may not be practical in at least some cases to have imaged markers visible in the breast image as they may detract from the clinical value of the x-ray image.

The new approach disclosed in this patent specification involves, as one alternative, forming a composite x-ray image of tissue and superimposed markers such that the markers are invisible in the composite image in a clinical setting but can be identified though computer-processing of the composite image. As another alternative, the markers are visible in the composite image. In either or both alternatives, the disclosed process and system further provide a way to remove contributions of the imaged markers from the composite image, if desired. "Invisible" in this patent specification means that the presence of imaged markers are not visible to an observer within the outline of a patient's breast in a realistic anatomical breast background under clinical x-ray dose, in typical clinical settings and in the type of visual examination of breast x-ray images that is done in conventional clinical screening and/or diagnosis. The approach disclosed in this patent specification is applicable to conventional mammography using flat panel or other digital imaging receptors, to digitized film, to tomosynthesis imaging using such receptors, and to other types of x-ray procedures and other x-ray imaging receptors, where it is desirable or helpful to accurately estimate the geometric thickness of the body or body part being x-rayed and to use the results to improve imaging or for other purposes.

A non-limiting example of the new approach uses one or more patterns of markers 22 that produce imaged markers 24 whose contrast relative to the breast image, or image of other body parties, can be so low that the imaged markers would not be seen in conventional assessment of x-ray images but can be detected through computer-processing of the images using techniques such as correlation analysis. This is made possible by using markers 22 that are in patterns with appropriate properties such as spatial distribution or other spatial and x-ray density properties as, for example, repeated line bars at known pitch. Correlation analysis of the imaged markers 24 then can allow detection of the position and pitch of imaged markers 24 in the composite markers/breast image. Once the geometry of the imaged markers 24 has been found, further computer processing can remove the contributions of markers 24 from the composite image. This removal can be so effective that an image that should be flat is in fact flat despite the presence of markers 22 at paddle 10. "Flat image" here means an x-ray image taken with a uniform phantom between paddle 10 and image receptor 20, i.e., and image that should have a uniform gray level within system tolerances and when viewed in typical clinical setting appears to be flat.

The effectiveness and robustness of the new approach can be demonstrated by experiments with a common ruler made of transparent plastic and having small painted black bars marking the millimeters (mm). In these experiments, the ruler is placed on paddle 10, and the ruler's mm marks serve as a pattern of markers 22. Breast phantoms of geometric thickness from 0 cm to 10 cm are immobilized between the paddle and the breast platform and are imaged under clinical x-ray dose levels in a mammography unit such as the system available in this country under the tradename Selenia™ from the assignee hereof, Hologic, Inc, of Bedford, Mass. Such experiments can demonstrate that geometric breast thickness can be calculated with errors within a ±1 mm range. Under clinical x-ray dose and realistic anatomical breast background, the imaged mm marks of the ruler are invisible to an observer. In a flat field image with a uniform phantom, the ruler image is faint but perceptible. However, additional computer processing as disclosed in this patent specification can remove this residue of the ruler image to thereby leave no visible artifacts in both flat field images and breast images. In similar tests with ⅒th to 1/20th of normal clinical x-ray dose, the ruler marks can still be identified through computer processing and breast thickness can be measured to within ±2 mm error range. This can allow geometric breast thickness to be computed from an x-ray image obtained with the AEC (automatic exposure control) scout shot, the very low dose x-ray shot typically taken for automatic exposure control purposes in mammography units such as the aforementioned Selenia™ system before actual beast imaging. The breast thickness calculated from the AEC shot information can then be used for more accurate AEC procedures to achieve better quality breast images than with less accurately determined geometric breast thickness, and/or for other purposes.

In the illustrative examples of FIGS. 1-4, five tiny bar markers 22 are used at paddle 10, uniformly spaced at a known pitch "d." They project in the image formed at receptor 20 as five similarly shaped imaged markers 24 that also are uniformly spaced but at an unknown pitch "D" As illustrated in FIG. 1, "h" is the distance between the focal spot 18 in x-ray source 16 and compression paddle 10, "H" is the distance from focal spot 18 and the image-plane of receptor 20, the breast thickness is designated "breast_thickness," and "s" designates the distance between the breast platform and the image plane. Parameters "d" and "H" and "s" are known, and parameter "D" can be determined as explained in this patent specification. Parameter h then can be calculated from the relationship h=(d/D)H, and breast thickness can be calculated as (breast-thickness=H−h−s). In this example, the centerline of the x-ray beam is normal to an centered at the image plane 20; however, if the centerline is at a different angle and point of incidence in the imaging plane, as in the case of some tomosynthesis projection images, a uniform ruler pattern as in FIG. 1 may be geometrically distorted. However, the distortion can be calculated at least approximately from knowing system geometry at the time the projection image is taken, e.g. from various encoders for the position of the x-ray source and from the construction of the system, so these geometric distortion can be effectively accounted for in the calculations disclosed in the patent specification.

In this alternative example imaged markers 24 would not be visible in a realistic breast image in a clinical setting, but to assist in the discussion below they are illustrated as visible in a composite marker/breast image in FIG. 2. Correlation processing can be carried out by shifting the image of FIG. 2 by a specified distance, e.g. to the right, adding the original and shifted images, then shifting the image of FIG. 2 again by the same distance and adding each shifted image to the result of the previous shift-and-add, etc., as long and the original and the last shifted images partially overlap. The shifting in general is not by an integer number of pixels so appropriate image interpolation can be carried out to generate the final shift-and-added image. The result of this shift-and-add process, or a normalized version thereof, can be expressed as amplitude related, for example, to an average attenuation or gray level of pixels in the summed images. This shift-and-add process is repeated for each of a number of different shift distances, e.g., for each of a progression of distances that differ in small steps and are in a reasonable range related to expected breast thickness ranges and taking into account possible magnification imaging in which the breast is spaced from platform 14 by a selected distance and, if desired, possible geometric distortions of pattern 22 because of factors such as a non-normal angle between the x-rays that form the image of a marker and the imaging plane. If the shift distance matches the actual pitch "D" of the imaged markers 24, the amplitude would be at a peak because the imaged markers 24 in effect line up and add while the rest of the composite x-ray image is more random and does not increase in amplitude as much. If the shift distance does not match the pitch "D," the amplitude resulting from addition is less because markers 24 are not aligned or at least not as aligned.

The shift-and-add process has been described qualitatively above, but in actual practice it can be performed by processing the pixel values of the composite markers/breast image. Consider the pixel values derived from receptor 20 representing pixels that are all within the middle imaged marker 24. After a single shift-and-add by "D," the pixel values contributed by the same marker 24 will be doubled; after another shift-and-add they will be tripled; and so on. However, if the shift is by a distance different from "D," at least some of the pixel values for the marker will not be doubled—they will be added to pixel values representing only the breast image. The pixel values for the entire composite image can be added or averaged, and the resulting amplitude should be highest for shift-and-add processes where the shift distance was "D." Preferably, the shift-and-add process is applied to one or more regions of interest (ROI) likely to contain imaged markers 24 rather than to the entire x-ray image. Many mathematical techniques are known for use in searching for weak but periodic signals, e.g. signals that are below a noise level of their environment. Such techniques generally involve some form of correlation analysis, and many correlation processes known in mathematics may be used in place of the shift-and-add example discussed in more detail in this patent specification. However, to the inventors' knowledge no such techniques have been applied in a process and apparatus as disclosed in this patent specification, e.g., for accurate determination of the geometric thickness of breast or other tissue being x-rayed and to use of the resulting information according to this patent specification.

A single pattern of markers can be used, or several patterns can be used at the same level or at different levels. While in these experiments a ruler mm marks are used as an example of a pattern, other patterns can be used so long an they have known geometries and are correlated, e.g., repeating at known pitch or otherwise correlated. While FIG. 1 illustrates a pattern 22 of only five bars, typically many more bars or other marks would be used. Only a selected part of the composite image can be processed that is likely to contain a significant portion of the pattern or patterns. For example, if one or more patterns are placed at the central portion of paddle 10, say 1 cm from the paddle edge that is pressed against the patients chest wall, then only a strip of the x-ray image that is likely to contain an image of that portion of paddle 10 can be computer-processed as described above. In addition, in cases where paddle tilting is deliberately provided, patterns or sub-patterns of markers 22 can be provided at different places of paddle 10, and the thickness of the immobilized breast can be calculated for the portion of the breast under each pattern and interpolated for other portions of the breast. The resulting information can be used to set exposure parameters and possibly for breast image processing purposes specific to respective portions of the imaged breast.

Figure 2:
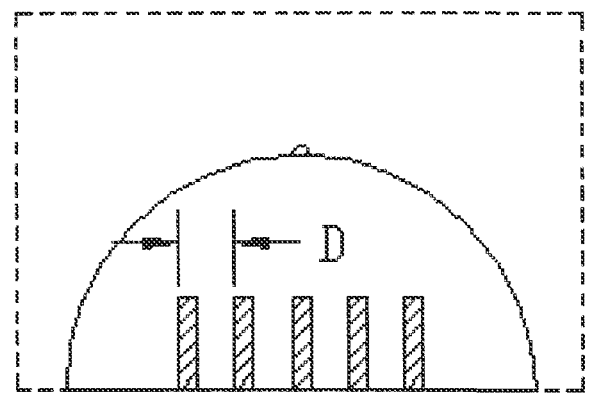
FIG. 2 illustrates a two-dimensional projection, such as a mammogram or a tomosynthesis projection image, containing a pattern of markers in the form of parallel bars or lines, where the imaged pattern has been emphasized for illustrative purposes but would be invisible in a clinical mammogram or other projection x-ray image.
Figure 3:
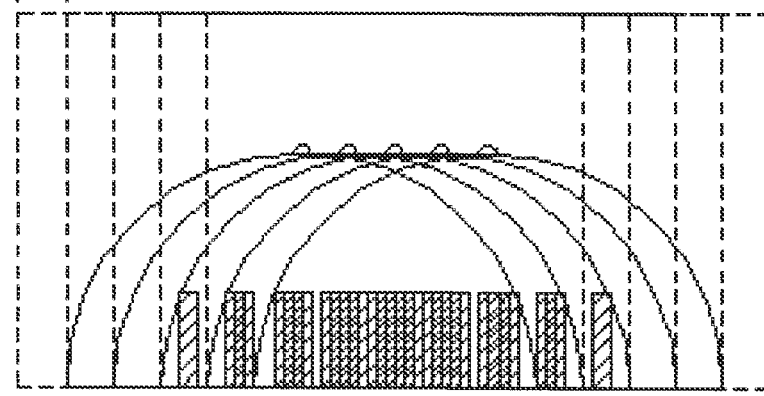
FIG. 3 illustrates an effect of shift-and-add correlation processing of the pattern of FIG. 2 where the shift distance does not equal the pitch, or separation distance, between the markers in the image.
Figure 4:
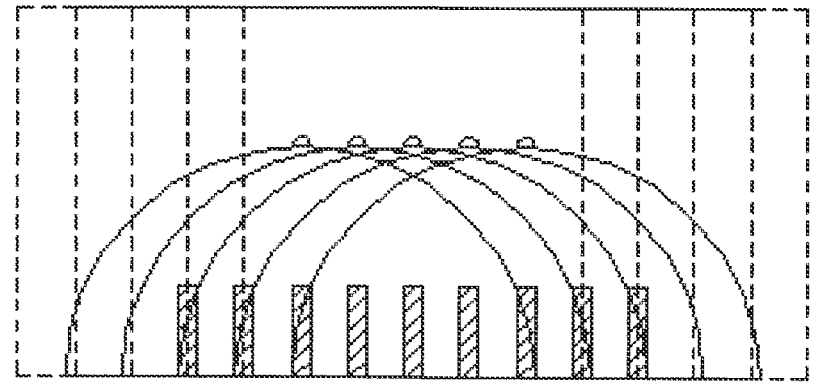
FIG. 4 illustrates an effect of shift-and-add correlation processing of the pattern of FIG. 2 where the shift distance equals the pitch of the markers in the image.

FIG. 3 shows four shifts of the image of FIG. 2 where each shift is by a constant distance that is not equal to the pitch "D." and FIG. 4 is a similar illustration but for shifts by a distance D. As seen, the imaged markers 24 are misaligned in FIG. 3 but not in FIG. 4, where the second marker from the left is the sum of marker 2 of the original image and marker 1 of the image after one shift by "D," etc.

An illustrative but non-limiting way to implement the process in practice involves the following basic steps:
  a. Compression paddle 10 is painted with markers 22 in a line bar pattern with a known bar pitch, e.g., 1 mm, as in a normal plastic ruler. Each line bar is about 6 mm long and is extends in a direction normal to the chest wall such that the bars are repeated along the chest wall direction in a mammographic or tomosynthesis procedure. Each paint line is thin, e.g., about 0.1 mm to 0.2 mm, for better correlation analysis. The contrast of the paint lines preferably should be low enough such that the imaged markers 24 in the composite marker/breast image are invisible when the composite x-ray image is viewed under typical clinical conditions;

b. Because the height of paddle 10 can be known to within about ±1 cm from conventional encoder information supplied in digital form to the system computer in a mammography unit such as the Selenia™ system, it can be calculated through basic trigonometric relationships approximately where the imaged markers 24 will be in the composite marker/breast x-ray image and approximately what the pitch will be of imaged markers 24. These calculations identify a region of interest (ROI) in the composite image that will likely contain imaged markers 24 or at least a good portion of the markers, and also identify a likely shift distance for the correlation analysis or at least a range of likely shift distances. In addition, if angular encoding is used to measure tilt of the paddle (see FIG. 15 and description thereof below) and several sub-patterns are used (as in FIG. 5c), the tilt information can be used to further refine the estimate of the likely location in the image of imaged markers of each sub-pattern, using known trigonometric relationships;

c. In one example of correlation image analysis, this ROI is shifted incrementally along the chest wall direction that is normal to line bars, with different shift amounts within the expected range, and the image resulting from the additions is checked for the line bar interference pattern;

d. Once the shift amount is equal to the line bar pitch, the resulting image will show strongly enhanced line bar patterns, say a factor of 50-100 times stronger relative to the background. In addition to shift-and-add along chest wall direction, all pixels along the 6 mm long line bar as imaged in the composite image are added. This can give another factor of 100-300 times more signal in the final line profile;

e. In frequency domain analysis, the strongest interference signal can be picked up at the expected frequency, and the corresponding shift amount can be found that is equal to the line bar spacing. From the measured pitch "D" of the imaged ruler markers at unknown height and the known pitch "d" of the ruler, the system magnification ratio can be calculated, and then the paddle height or breast thickness is derived at the ROI region. If multiple clusters or sub-patterns of line bars are placed at paddle 10, the analysis can be repeated to get the paddle height profile and breast thickness at each ROI within the whole detector area, and to calculate paddle tilt angle or regional deformations as well;

f. The process incorporates principles similar to those used in the design of a "phase lock amplifier" in analog electronics to identify a weak electronic signal of known frequency in the time domain. Similar principles can be used in the spatial domain as a form of a "phase lock amplifier" to measure a spatial frequency in an x-ray image;

g. Once the pitch of imaged markers 24 and the paddle height are calculated, the location and the signal magnitude of imaged markers 24 in the composite marker/breast image can also be found through conventional trigonometric relationships. Additional artifact correction algorithms can therefore be applied to remove the residue signal of the ruler marks (imaged markers 24) from the composite image, which will make the ruler marks become completely or essentially invisible even in the flat field image of the ruler. After such removal of imaged marker contributions, the x-ray images can be more suitable for processing such as CAD (computer aided detection) analysis.

Figure 5A:
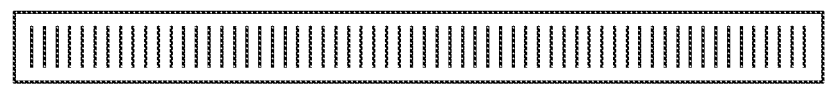
FIG. 5a illustrates a ruler pattern that can be used to verify an example of the process disclosed in this patent specification.
Figure 5B:
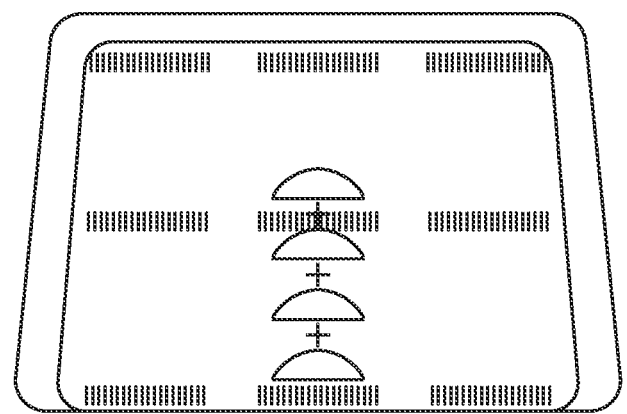
FIG. 5b illustrates a top view of a compression paddle in current public use in mammography systems offered by the assignee hereof, with automatic exposure control (AEC) markers that are not visible in a clinical image.

FIG. 5a shows a magnified ruler pattern that can be used in the experiments referred to above. As seen, the ruler pattern has mm marks. The pattern was printed, using a laser printer, onto a thin sheet of plastic, but can be provided by other printing techniques, or can be engraved into the paddle, or can be formed in some other way, so long as it has the required x-ray properties that would cause imaging the pattern into a composite pattern/breast image as an imaged pattern that is invisible within the breast outline when viewing the composite image in clinical settings or, in alternative embodiments, the imaged pattern is visible if the composite image is viewed in clinical settings. Optionally in either alternative, contributions of imaged markers can be removed from the composite x-ray image through further computer processing. FIG. 5b shows a typical compression paddle 10 that can be used with a Selenia™ mammography system, with painted marks related to AEC features, which AEC marks are not visible in the breast x-ray image in clinical settings though they can be clearly seen on the paddle. FIG. 5c illustrates the paddle of FIG. 5b with an attached plastic sheet containing ruler patterns similar in principle to that of FIG. 5a but the patter in FIG. 5c is in the form of nine different sub-patterns of ruler marks, where both the AEC marks and the imaged ruler marks of the sub-patterns are visible on the paddle but can be invisible when imaged in a breast x-ray image in a clinical setting. For clarity, the marks of the nine sub-patterns shown in FIG. 5c are coarser and the parallel lines are fewer in number in each sub-pattern than they typically would be in actual practice. While the sub-patterns are shown as extending only in the lateral direction, in practice the sub-patterns may extend in different directions that can differ between sub-patterns. And, the sub-patterns need not be in the form of ruler marks, as discussed in more detail below and different sub-patterns can have different marks in different arrangements.

FIG. 6a illustrates results of experiments using a paddle 10 with a superimposed ruler pattern as seen in FIG. 5c immobilizing a 4.5 cm BR50/50 breast phantom, and FIG. 6b is similar but illustrates results when using a 4.5 cm cadaver breast phantom, in each case with the use of a Selenia™ mammography system. Strip 1 of FIG. 6a illustrates an x-ray image (actually a strip taken from an image) that contains the combined contribution of the breast phantom and the ruler mm marks serving as a pattern of markers 22. The imaged markers 24 are not seen in strip 1 in a typical observation in clinical settings. Strip 2 illustrates the same image but with imaged markers 24 removed using the process disclosed in this patent specification. No difference can be seen between strips 1 and 2 in typical clinical setting observations. Strip 3 illustrates a difference image obtained by subtracting the images of strips 1 and 2 from each other. As expected, the imaged markers 24 can be seen in this difference image, demonstrating that there is information about markers 24 in the image of strip 1. Strip 4 illustrates the result of a shift-and-add operation on the image that contains strip 1, using a shift distance that matches the actual pitch of imaged markers 24. The shift-and-add operation reinforces and emphasizes imaged markers 24, making them visible in the composite x-ray image and thus in another way demonstrating that they are present in the composite image that contains strip 1. In practice, this process detects the interference signal due to the presence of markers 24 in the composite image of strip 1. Strip 5 illustrates the result of a shift-and-add operation on the image of strip 2, carried out in the same way as the one that produced strip 4. However, imaged markers 24 are not seen in strip 5, demonstrating that image 2 was in fact pattern-corrected by removing essentially all the contributions of the imaged marker 24 from the composite image of strip 1. FIG. 6b has corresponding respective strips 1-5 but pertains to imaging a cadaver breast phantom.

Figure 7A:
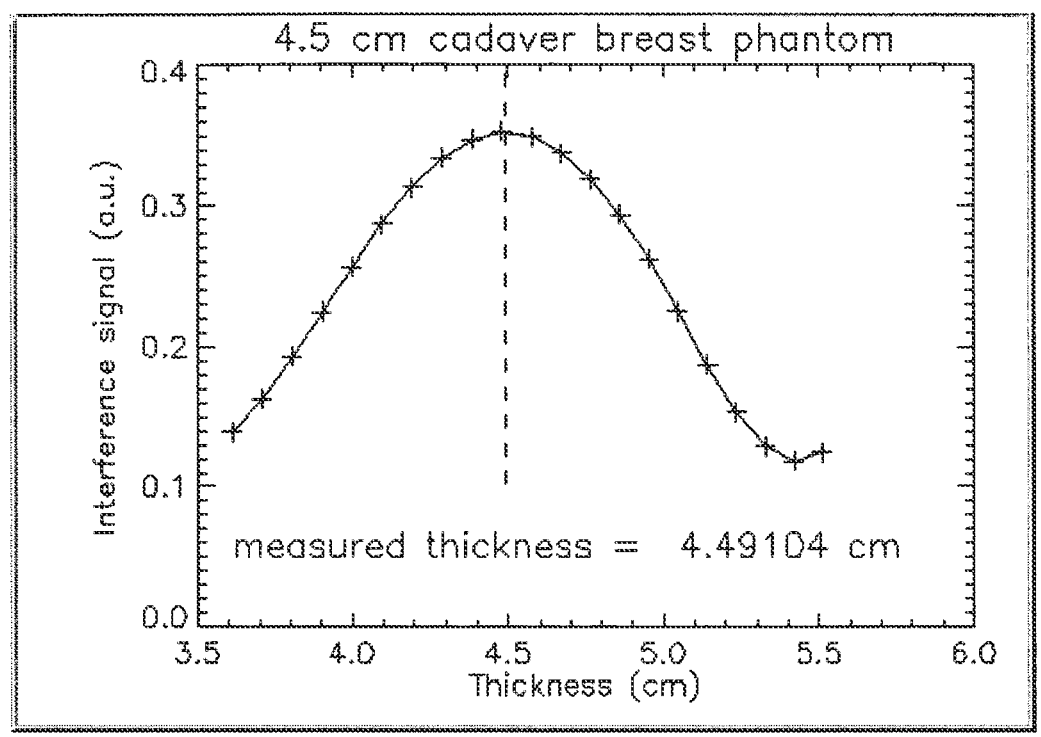
FIG. 7a is a graph illustrating an example of amplitude variations of an interference signal as in FIG. 6b (strip 4) vs. estimated compression paddle height above a breast plate at normal 1× clinical x-ray dose. The true height of the compression paddle was 4.5 cm, and the measured height using the methods disclosed in this patent was 4.49 cm, identified through the peak of the curve in FIG. 7a. The interference signal amplitude peaks at a point within 0.01 cm of the paddle height.
Figure 7B:
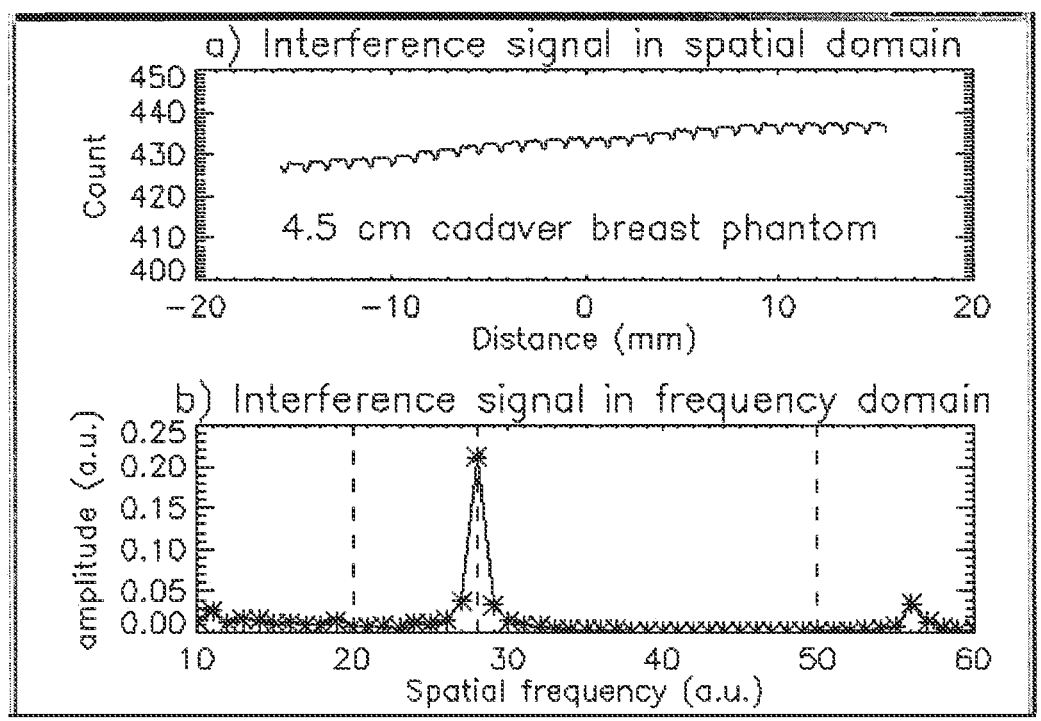
FIG. 7b illustrates the interference signal from a specific shift-and-add image in the same example, as an averaged signal plot in the spatial domain in the upper plot and in the frequency domain in the lower plot, after frequency analysis of the spatial domain plot through FFT (Fast Fourier Transform) analysis.
Figure 8A:
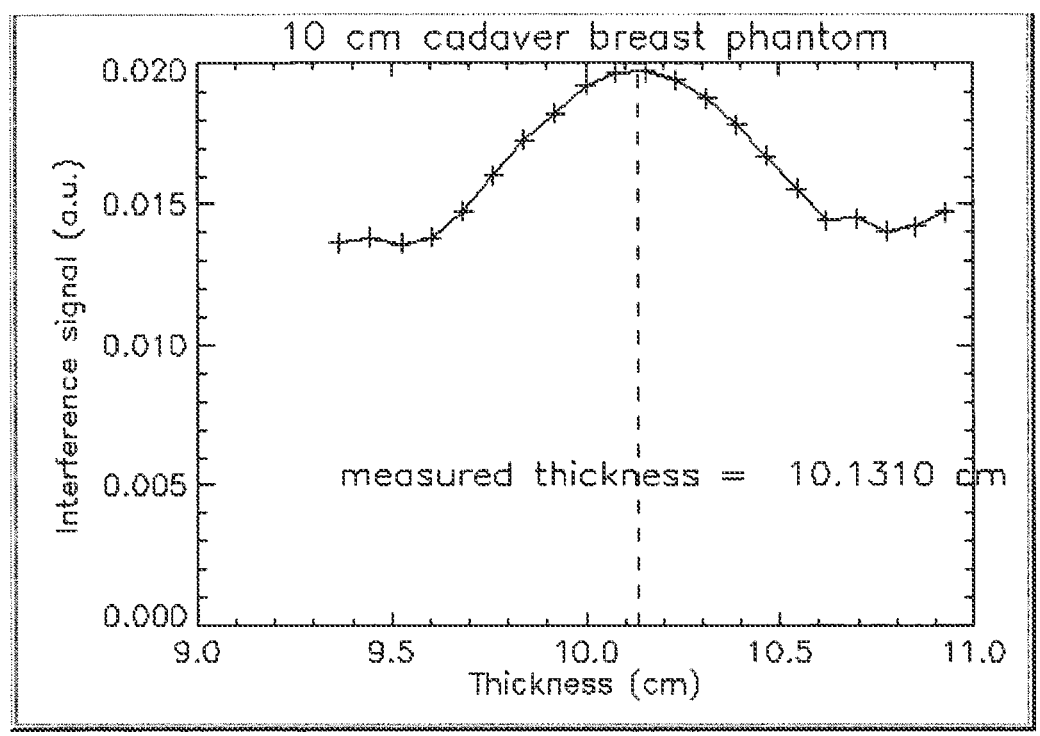
FIG. 8a is a graph illustrating an example of amplitude variations of an interference signal as in FIG. 6b (strip 4) but with a 10.0 cm thick cadaver phantom vs. compression paddle height at $\frac{1}{15}^{th}$ of a normal 1× clinical x-ray dose. The true height of the compression paddle was 10.16 cm, and the measured height using the methods disclosed in this patent was 10.13 cm. The interference signal amplitude peaks at a point within 0.2 cm of phantom thickness.
Figure 8B:
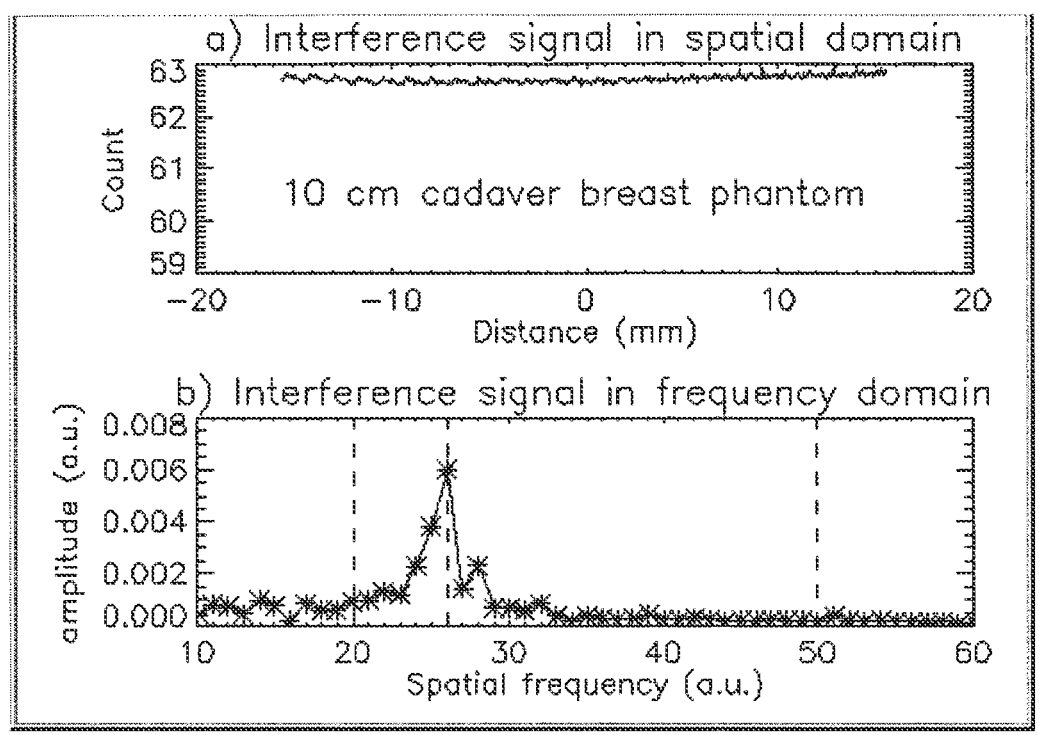
FIG. 8b illustrates the interference signal from a specific shift-and-add image in the same example, as an averaged signal plot in the spatial domain in the upper plot and in the frequency domain in the lower plot, after frequency analysis of the spatial domain plot through FFT (Fast Fourier Transform) analysis.

FIG. 7a shows a plot of an amplitude of the interference pattern of imaged markers 24 (seen in FIG. 6a, strip 3) versus different shift distances and also shows the measured breast thickness values, in the case of using a 4.5 cm thick cadaver breast phantom and normal x-ray imaging dose for mammography. Each of the data points is for a different shift distance. The peak signal amplitude corresponds to calculated breast thickness. As seen in FIG. 7a, the calculated breast phantom thickness is within 0.01 cm of the 4.5 cm phantom thickness. The upper plot in FIG. 7b illustrates for the geometry of FIG. 7a an averaged interference signal in the spatial domain of imaged markers 24 from one specific shift-and-add image shown in strip 4 of FIG. 6b. The lower plot in FIG. 7b shows results from FFT (Fast Fourier Transform) analysis, including a peak signal at the expected spatial frequency. FIGS. 8a and 88 are similar plots, respectively, but for the case of using a 10.0 cm thick cadaver phantom and $\frac{1}{15}^{th}$ of normal x-ray dose for mammography. The amplitude of the interference signal (peak-to-background) is reduced about 40 times relative to the case of FIG. 7a (from about 0.2 to about 0.006) but the process disclosed in this patent specification can still detect this weak pattern signal and calculate breast phantom thickness to within 0.2 cm of the 10.0 cm phantom thickness, demonstrating the high robustness of the process.

Figure 9:
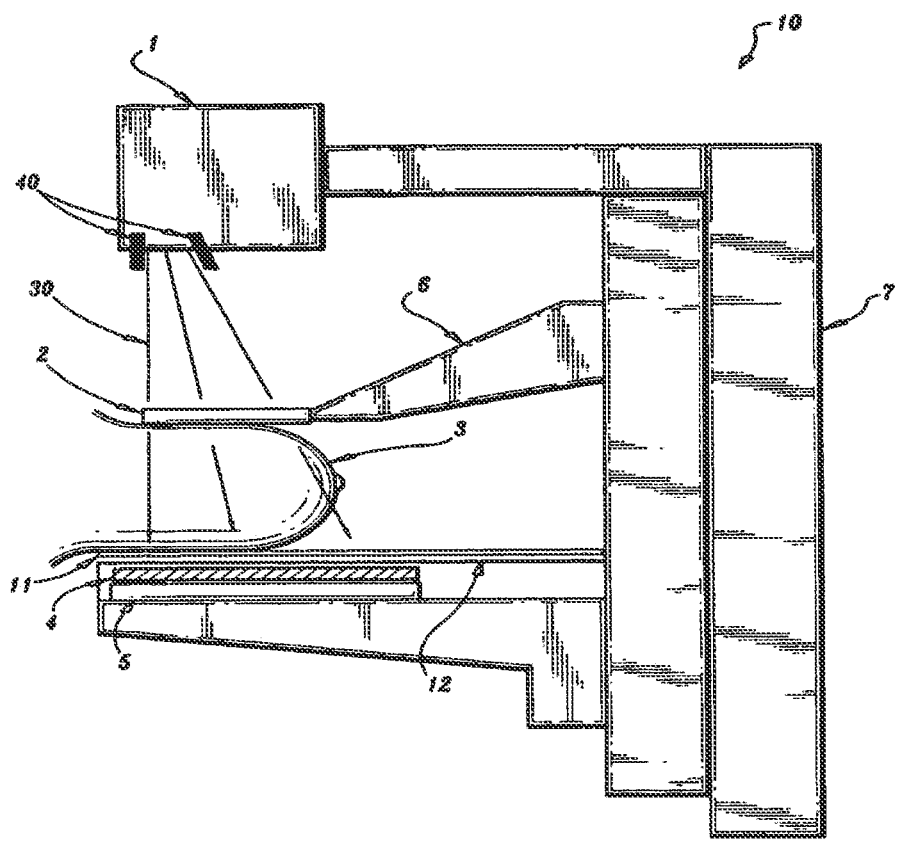
FIG. 9 is a partial side view of a mammography system in which a patient's breast is immobilized between a compression paddle and a breast platform and is imaged on a flat panel digital imager, with or without the use of an anti-scatter grid, in accordance with one embodiment of the system and method disclosed in this patent specification.
Figure 10:
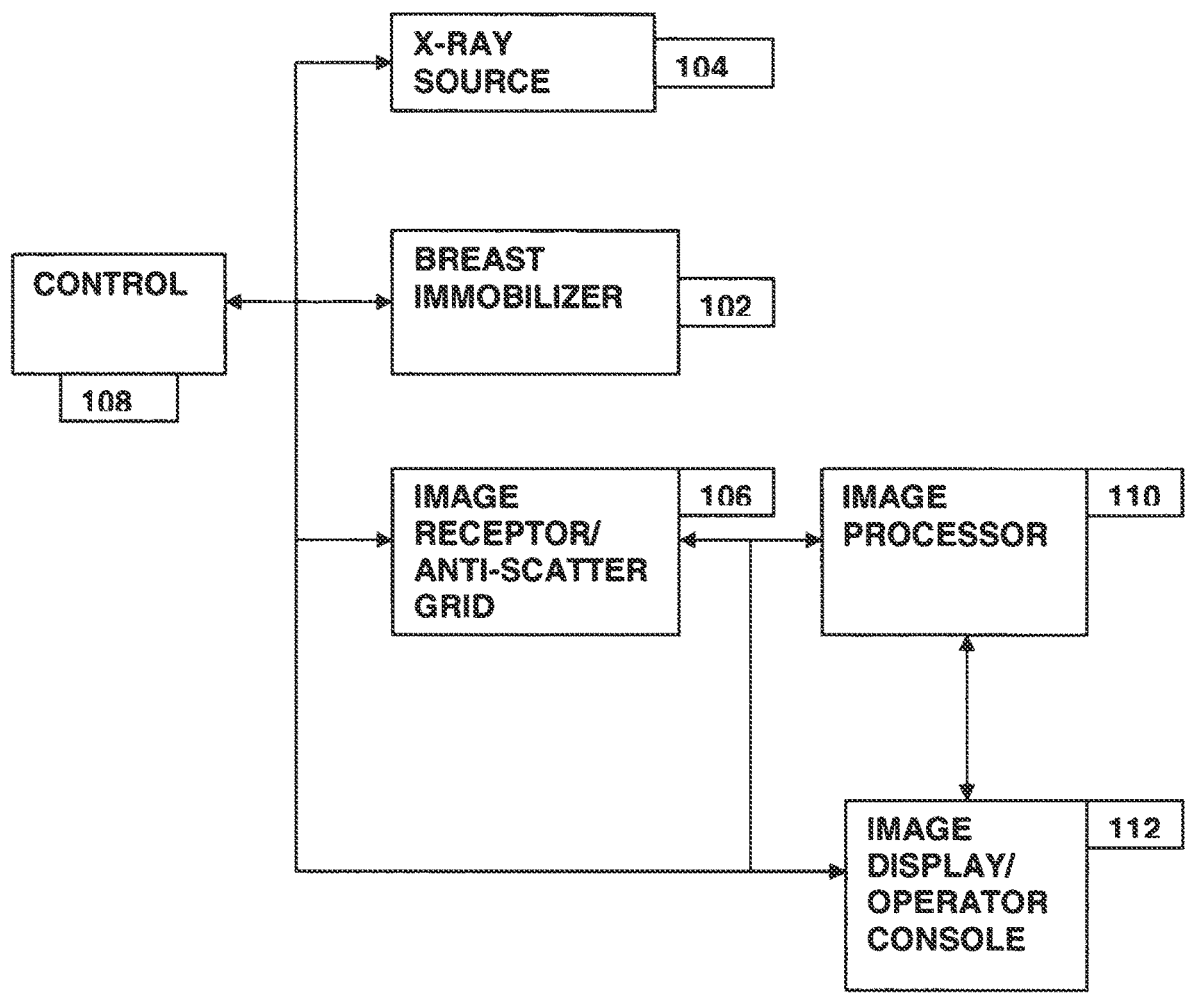
FIG. 10 is a block diagram illustrating main portions of a system in which the disclosed process is used.

FIG. 9 illustrates certain components of a system that can be used for mammography or tomosynthesis, in each case using the process of determining breast thickness and using the result to improve breast imaging. An x-ray source 1 is at one end of a generally C-shaped frame 7 and a flat panel digital x-ray imaging receptor 5 is at the other end. X-ray source 1 includes a collimator schematically illustrated at 40 to confine an x-ray beam 30 emitted from source 1 to a desired footprint at receptor 5, typically no larger than the area of receptor 5 and preferably just enough to image a patient's breast 3 or at least a selected part thereof, as compressed toward receptor 5 by a compression paddle 2 mounted on an arm 6 that in turn mounts to frame 7. A lower platform 11, often called a breast tray or platform, is immediately below the breast, and a scatter-reducing grid 4 is between breast tray 11 and x-ray receptor 5 and is housed in the same enclosure 12 with the receptor. As is known in the art, frame 7 can rotate between horizontal and vertical directions of x-ray beam 30. In use for a CC view, paddle 2 and its supporting arm 6 are moved up, breast 3 is positioned on tray 11 and compressed by bringing paddle 2 down as needed. With suitable collimation by collimators 40 (which typically collimate in two directions, of which only one is illustrated in FIG. 9), beam 30 from source 1 images the breast onto receptor 5 and the resulting electronic image information is transmitted to a viewing station 112 (FIG. 10). The image typically is rectangular. Preferably, the collimation is such that beam 30 illuminates an area of receptor 6 just large enough to show the image of breast 3, or at least a selected part thereof. Different sizes and shapes of paddles 2 can be mounted to arm 6, and the paddle can be selectively positioned off-center relative to proximal edge Sa of receptor 5 (the left edge in FIG. 9). For mammography, grid 4 can be in the position shown in FIG. 9. For tomosynthesis data acquisition, grid 4 can be retracted to the right of FIG. 9 and out the path of x-rays 30, and a number of projection breast images can be taken at different angles of the x-ray beam relative to the breast and processed to derive tomosynthesis slice images. Paddle 2 of FIG. 9 can be provided with one or more patterns or sub-patterns of markers 22 as with paddle 10 of FIG. 1. Breast platform 11 and receptor 5 of FIG. 9 correspond to platform 14 and receptor 20 of FIG. 1.

A system that embodies an example of the new approach to finding and using geometric breast thickness is illustrated in block diagram form in FIG. 10. The system can be a mammography system, or a tomosynthesis system, or a fusion system that can be used for either or both purposes. A beast immobilizing device 102 is between an x-ray source 104 and an image receptor/grid unit 106. Device 102 can comprise paddle 10 and breast platform 14 of FIG. 1, or paddle 2 and breast platform 11 of FIG. 9. Unit 104 can comprise source 16 and focal spot 18 of FIG. 1, or source 1 and collimator 40 of FIG. 9. Unit 106 can comprise receptor 20 of FIG. 1 or the combination of receptor 5 and grid 4 or FIG. 9. A control unit 108 is coupled with units 102, 104 and 106 to control their operation and to send and receive information regarding their operation. An image processor 110 is coupled with unit 106 to receive image data therefrom and exchange control and other information therewith, and also is coupled with unit 108 to exchange control and other information. A display/operator console unit 112 is coupled with image processor 110 and control 108 to exchange display and other information therewith, and to display images provided by unit 112 and receive user input through appropriate interface devices. The units illustrated in FIG. 10 can include the functionalities of the corresponding units of the commercially available Selenia™ mammography system as well as the additional processing functionality to carry out the process of determining breast thickness and using the result for AEC and/or other purposes. The additional processing functionality can further include breast density calculations that use information regarding the geometric thickness of the breast as imaged at one or more regions of the imaging receptor.

An initial application of the disclosed method and apparatus is to provide accurate estimates of breast thickness in mammography and/or tomosynthesis systems using the AEC scout view before the main exposure and to use the thickness information to set x-ray technique, to provide accurate estimates of breast thickness for more accurate breast density calculations, and for other purposes such as control over tomosynthesis slice image reconstruction and display. In tomosynthesis, the thickness information from a projection image can be used in AEC for other projection images and/or in AEC for a subsequent mammogram taken in the same breast compression in the same system. Similarly, the thickness information from a mammogram can be used in AEC for taking subsequent tomosynthesis views or other x-ray images taken in the same breast compression in the same system. Another use of the process and apparatus for compositing invisible or visible markers into an x-ray image and if desired removing such imaged markers through further processing is in digital encoding of selected information into an x-ray image. The composited marker information can be used for a wide variety of purposes such as identifying the patient, the procedure for acquiring the data for the image, encoding other information regarding the image, or for providing any other type of information embedded by way of invisible markers. A similar process and apparatus can be used in other x-ray procedures to determine the geometric location or thickness of the body or body part being x-rayed, as in bone densitometry and general radiography. Still another use of the disclosed process and apparatus is for registering mammograms or other x-ray images, where the imaged markers that can be visible or invisible, as appropriate for a particular application, can be used as registration marks that can be left in the registered images when they are invisible in normal observation and this is desirable, or can be left as visible marks, or can be removed in either case through further processing as described above. As one non-limiting example, the breast thickness calculated as described in this patent specification can be displayed separately from or together with the breast x-ray images, e.g., can be displayed to the technician operating a system such as Selenia™ on a numerical display.

Figure 11:
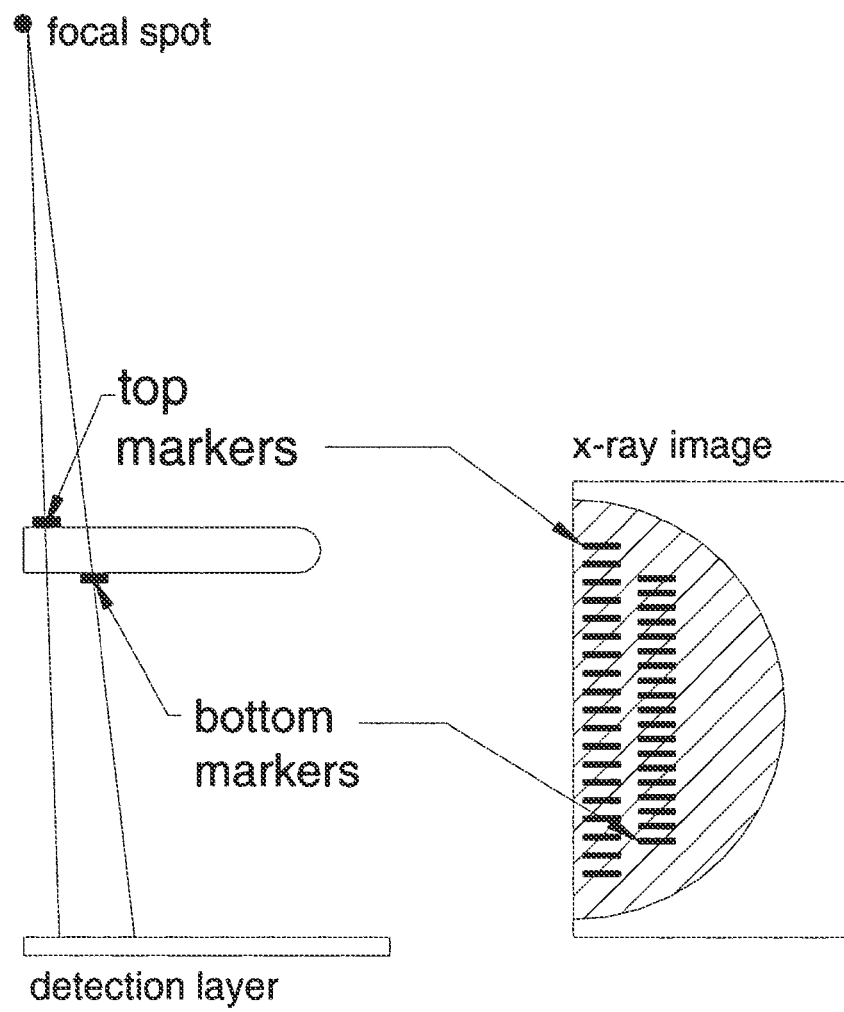
FIG. 11 illustrates an example using two sets of markers, at different heights above an imaging plane (detection layer) that can facilitate calculation of the heights, and illustrates an x-ray image showing the imaged markers (that would not normally be visible in a clinical image)

Other examples of applications of the new approach include using two of more patterns of markers, for example using two patterns or sub-patterns as illustrated in FIG. 11, where one pattern is above the patient's breast and another is below the breast, such that the two patterns do not overlap or only partly overlap in the composite x-ray image. The upper pattern an be on the otherwise conventional compression paddle of a mammography/tomosynthesis system and the lower pattern can be on the top surface of an otherwise conventional magnification table that is placed between the breast and the breast platform when it is desired to magnify the breast x-ray image. FIG. 11 includes an illustration to the right of a composite x-ray image that would result from using two examples of such patterns. The markers in one alternative embodiment would not be visible when viewing the image in a clinical setting. In another alternative embodiment, the imaged markers can be visible (when appropriate patterns 22 are used) and can be removed when it is desired to view the composite x-ray image without visible residue of imaged markers.

Figure 12:
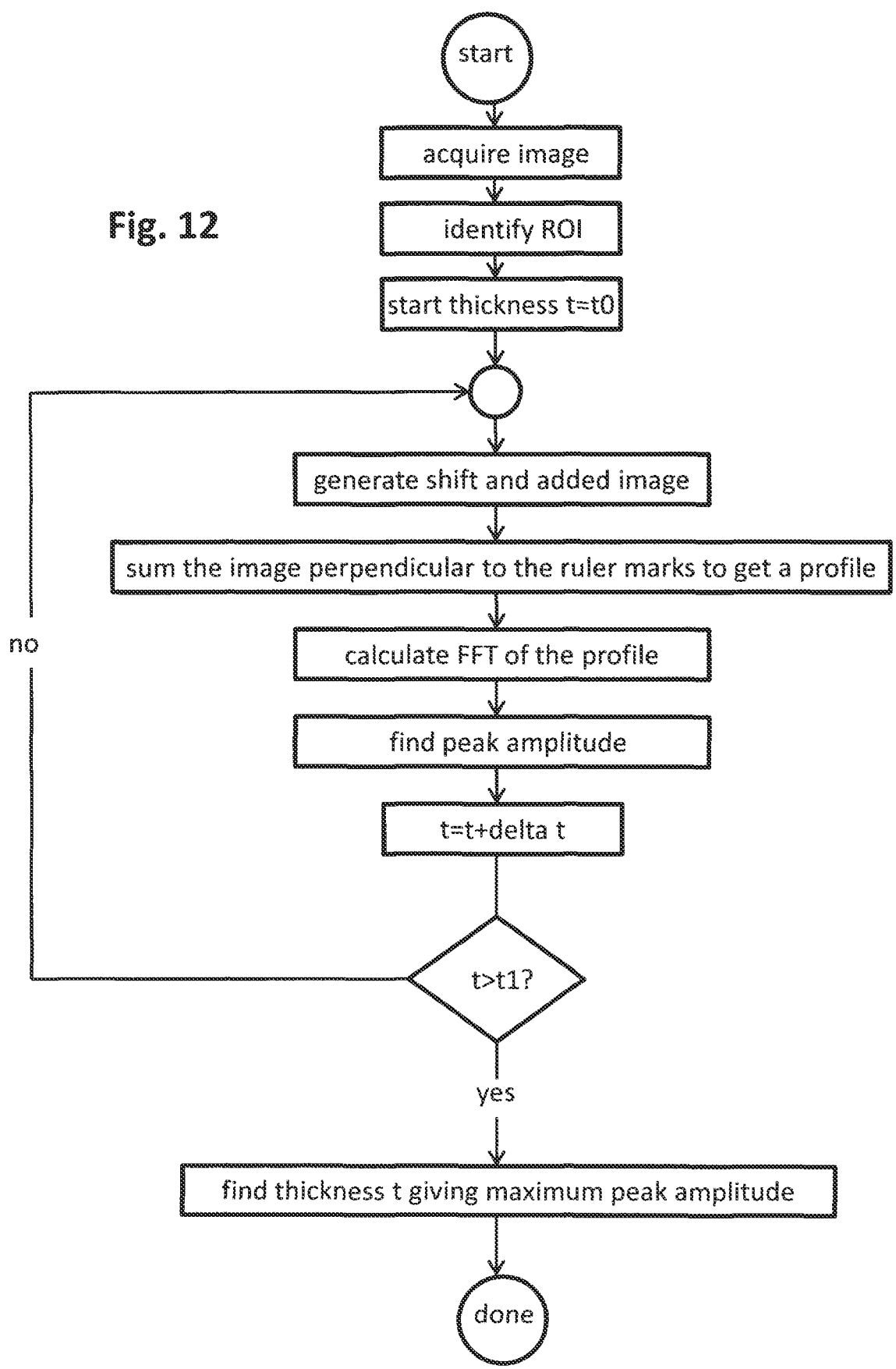
FIG. 12 is a flowchart illustrating steps in a process of estimating height of objects with markers.
Figure 13:
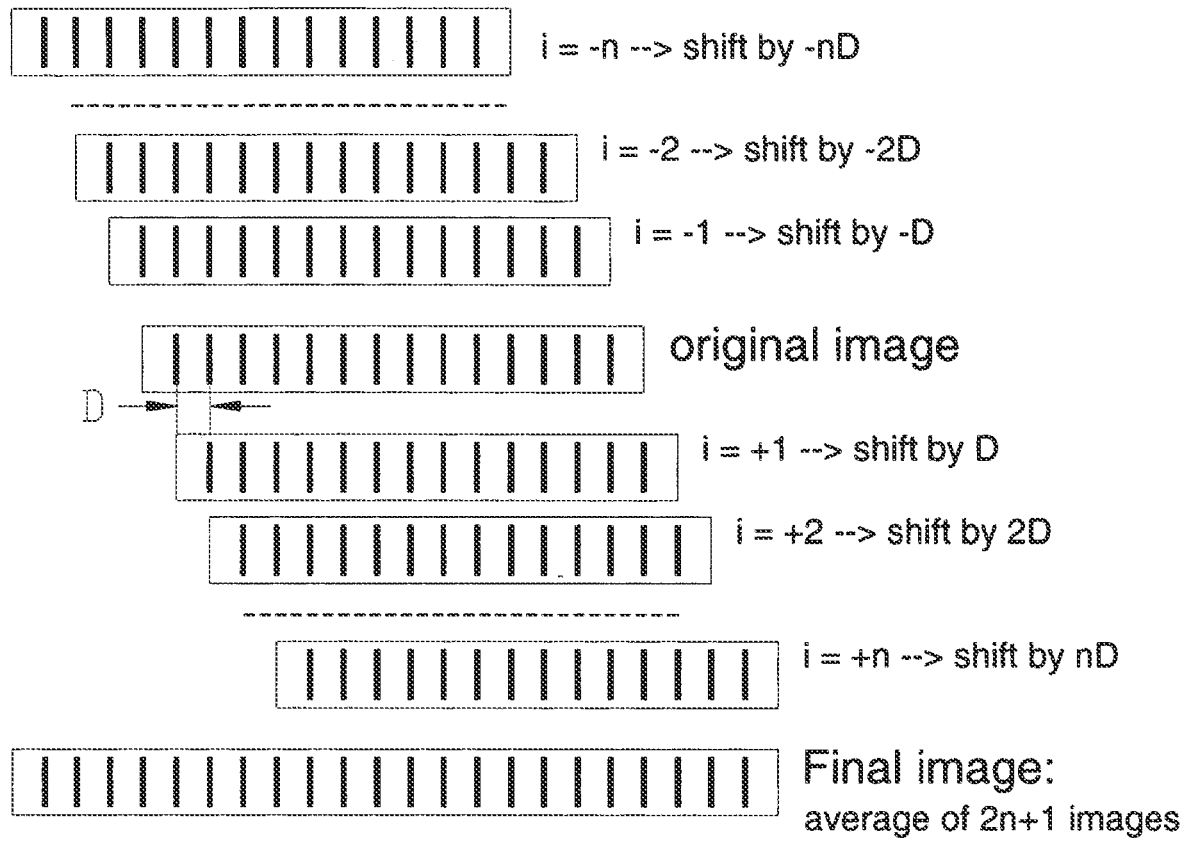
FIG. 13 illustrates shift-and-add according to the flowchart of FIG. 12.

FIG. 12 is a flowchart illustrating one example of a process according to the new approach disclosed in this patent specification, and shows the following main steps of a process for calculating the thickness of an object that is between an upper and a lower plane and is being x-rayed. At least one pattern of markings is present at least at one of the upper and lower planes. In a non-limiting example, the upper plane can be at a compression paddle and the lower surface at a breast platform in a mammography/tomosynthesis system. The main steps can be:

a. Acquire the x-ray image, with a pattern of markers imaged within the field of view, e.g., as illustrated in FIG. 1 or 11;
b. Identify the approximate region of interest (ROI) where the imaged markers are approximately expected in the x-ray image. This can be derived through conventional calculations from knowing the locations of the pattern (s) relative to the acquisition geometry, including from a conventional encoder providing information regarding the approximate height of a compression paddle;
c. Start the calculation at an estimated thickness $t=t_0$ that is less than the true thickness of the object. If the system reports an approximate thickness of the object using, for example, an encoder for paddle height, the encoder value can be used. For example, if the encoder reports the paddle height is 5 cm, a starting height could be 4 cm. If there is no known estimate for the true paddle height, the starting height could be zero;
d. Generate a shift-and-added x-ray image. The amount of shifting per image is determined from the thickness t being estimated, and from system geometry, e.g., according to the expressions relating thickness to known parameters discussed above in this patent specification;
e. Generate a profile by summing the image in a direction perpendicular to the lengths of the imaged markers;
f. Calculate the one dimensional FFT of the profile;
g. Find the amplitude of the peak;
h. Increment to the next thickness to test. Typical increments depend upon the desired final thickness measurement accuracy, and for digital mammography/tomosynthesis can be, as a non-limiting example, in the range of about 0.1 mm to 1 mm;
i. If the thickness is less than the desired maximum thickness to test, repeat at step d.;
j. Now find the thickness that generated the largest peak amplitude in step g. This thickness is the calculated thickness of the object according to the pattern above the object. Similar processes can be used if the parameter to be calculated is the position in space or with respect to another portion of the system, of the upper or lower patterns of markings, or the difference in position between the two patterns of markings, or if a parameter is sought that is related to the position in space or in relation to a system component, or each or two or more patterns of markings that are approximately at the same level, such as two or more patterns on a compression paddle that might tilt or deform in the course of compression.

The process described immediately above can be adapted to the more general case where it is desired to calculate the position in space of one or more patterns of markings that are between an x-ray source and an image plane of an x-ray imaging receptor.

Figure 14:
FIG. 14 illustrates two different patterns of markings: a pattern "a" in the form of a regular pattern of parallel short lines and a pattern "b" that can be arbitrary and can even be random or pseudo-random, so long as it has characteristics that can differentiate it from a background x-ray image to which it contributes.
Figure 14:

FIG. 14 illustrates an upper pattern of markings "a" that is similar to the patter in FIG. 5a and to a sub-pattern of FIG. 5c, and a lower pattern of markings "b" consisting of the lines of pattern a broken down into four rows each consisting of much shorter lines. Because any arbitrary pattern whose general shape of certain other properties are known can be detected in the x-ray image through spatial domain correlation processes (without FFT) as long as the imaged pattern has enough signal, the arbitrary pattern can be found with sufficient accuracy according to the approach disclosed in this patent specification. Even a random or pseudo-random pattern of small areas in the composite x-ray image can be detected if it has properties that generally distinguish it from the image of a breast or other object in the composite x-ray image. One example of such characteristics can be edges that are too sharp and appear too frequently to belong to an image of a breast or another object. In the example of pattern b in FIG. 14, The x-ray imaged rows of shorter lines of pattern b can be shifted relative to each other through computer processing in a direction perpendicular to their lengths to conceptually collapse them into pattern "a." As long as pattern b has approximately the same number of pixels as pattern "a," it can be found nearly equally well in the composite x-ray image. Pattern b need not consist of short lines; other shapes can also work. A pattern such as V can ensure invisibility in the composite x-ray image more reliably and under more relaxed viewing conditions.

Figure 15:
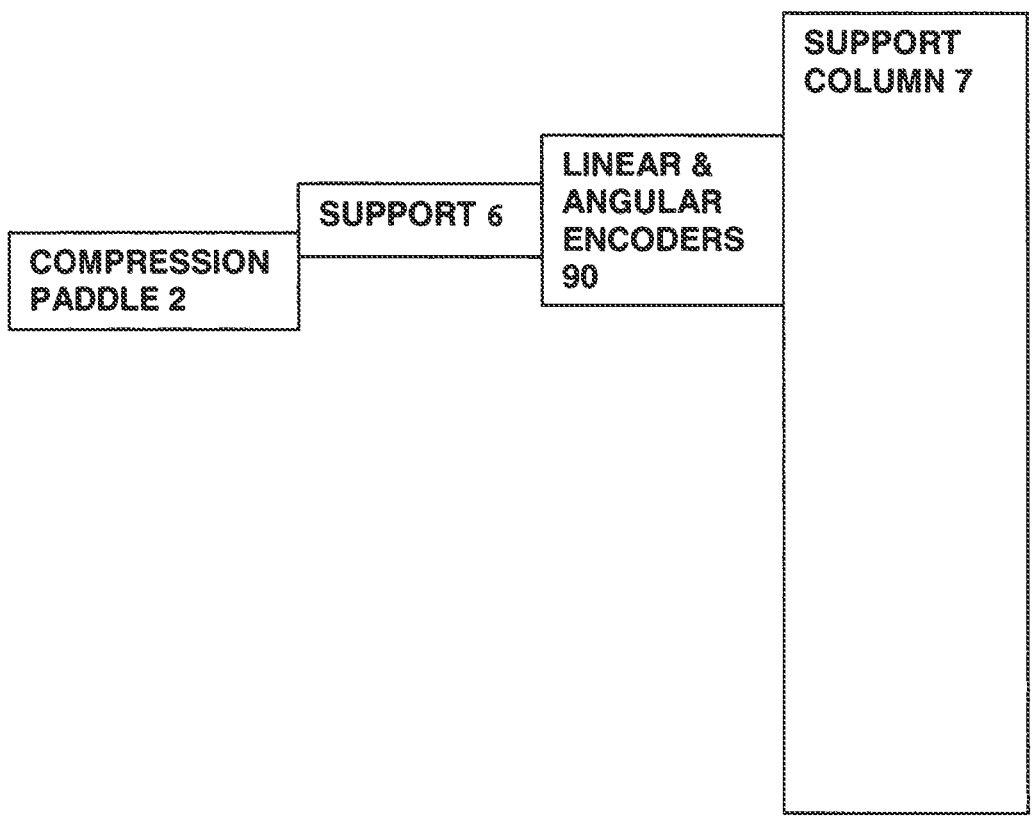
FIG. 15 is a schematic illustration of another way of measuring both height and tilt of a compression paddle.

FIG. 15 schematically illustrates measuring not only the height of a compression paddle such as paddle 2 of FIG. 9 but also tilt of the paddle as it compresses the patient's breast against breast platform 12. As illustrated, support 6 for paddle 2 is coupled with linear and angular encoders 90 in addition to being supported for vertical motion along column 7. The linear encoder can be an optical encoder or an encoder as used in the Selenia™ system available from the common assignee. The angular encoder can be any suitable optical encoder or a resolver that can measure the angle of paddle 2 relevant to a reference as the paddle compresses the patient's breast and tilts from a plane parallel to breast platform. Both the linear and angular encoders provide digital information to control 108 and image processor 110, which information can be used as discussed above to assist in identifying regions of interest to which correlation processing can be applied. A linear encoder of this type has been in public use in this country for more than a year. An angular encoder for breast compression paddle that provides digital information to a control such as 108 has not been in public use but a mammography system with a built in potentiometer that is not providing digital information and is not used to measure tilt and provide it for use in the system has been in systems shown in at least one trade show in this country.

Software that controls the process described above can be stored in a tangible computer readable storage medium to be used as a computer program product and/or can be transmitted via a computer network or other transmission medium.

The above specific embodiments are illustrative, and many variations can be introduced on these embodiments without departing from the spirit of the disclosure or from the scope of the appended claims. For example, elements and/or features of different examples and illustrative embodiments may be combined with each other and/or substituted for each other within the scope of this disclosure and appended claims. As one of many examples, the processes disclosed and claimed in this patent specification can be applied to CR based x-ray imaging, where the charge storage phosphor or x-ray detection material is not rigidly fixed in relative to the breast platform, or similarly to digitized film images.

The invention claimed is:

1. A system for imaging a breast, the system comprising:
an x-ray source comprising a focal spot;
an imaging receptor comprising an imaging plane disposed at a known distance from the focal spot; and
a paddle configured to be movably disposed between the x-ray source and the imaging receptor, the paddle comprising:
   a breast-contacting surface; and
   a first sub-pattern of markers disposed at a first predetermined distance from the breast-contacting surface;
   a second sub-pattern of markers disposed at a second predetermined distance from the breast-contacting surface;
at least one processor; and
a memory storing instructions that, when executed by the processor, cause the system to perform a set of operations comprising:
   concurrently x-ray imaging the paddle and the breast disposed between the breast-contacting surface of the paddle and the imaging receptor;
   obtaining an x-ray image depicting the breast, the first sub-pattern of markers superimposed on the breast, and the second sub-pattern of markers superimposed on the breast;
   identifying a first region of interest in the x-ray image that corresponds to the first sub-pattern of markers and identifying a second region of interest in the x-ray image that corresponds to the second sub-pattern of markers; and
   processing the first region of interest and the second region of interest to determine geometric information regarding the first sub-pattern of markers and the second sub-pattern of markers.

2. The system of claim 1, wherein the set of operations further comprises processing the geometric information of the first sub-pattern of markers and the second sub-pattern of markers to obtain information regarding the paddle.

3. The system of claim 2, wherein the information regarding the paddle comprises at least one of a paddle deformation, a paddle orientation, and a paddle height.

4. The system of claim 2, wherein the information regarding the paddle comprises an angle of the breast-contacting surface relative to the imaging plane.

5. The system of claim 1, wherein each of the first sub-pattern of markers and the second sub-pattern of markers comprise a plurality of ruler marks.

6. The system of claim 1, wherein each of the first sub-pattern of markers and the second sub-pattern of markers are spaced apart at a known pitch.

7. The system of claim 1, wherein the first sub-pattern of markers are disposed parallel to the second sub-pattern of markers.

8. The system of claim 7, wherein the first sub-pattern of markers are disposed substantially parallel to a chest wall of a patient.

9. The system of claim 1, wherein the set of operations further comprises processing the geometric information of the first sub-pattern of markers and the second sub-pattern of markers to obtain information about the breast.

10. The system of claim 9, wherein the information about the breast comprises a first thickness of the breast proximate the first sub-pattern of markers and a second thickness of the breast proximate the second sub-pattern of markers.

11. The system of claim 9, wherein the information about the breast comprises a deformation of at least a portion of the breast.

12. The system of claim 1, wherein when the breast-contacting surface is in contact with the breast, the first sub-pattern of markers and the second sub-pattern of markers are disposed at substantially a same distance from the imaging receptor.

13. The system of claim 1, wherein when the breast-contacting surface is in contact with the breast, the first sub-pattern of markers and the second sub-pattern of markers are disposed at substantially a same distance from the breast-contacting surface.

14. The system of claim 1, wherein the paddle further comprises a plurality of automatic exposure control marks.

15. The system of claim 14, wherein the plurality of automatic exposure control marks are disposed on a first portion of the paddle and the first sub-pattern of markers are disposed on a second portion of the paddle.

16. The system of claim 1, wherein the paddle is at least partially rigid.

17. The system of claim 16, wherein the paddle is rigid.

18. The system of claim 1, wherein each of the first sub-pattern of markers and the second sub-pattern of markers are identical in a width dimension and a length dimension.

* * * * *